(12) United States Patent
Gitman et al.

(10) Patent No.: US 10,940,086 B2
(45) Date of Patent: Mar. 9, 2021

(54) BOTTLE SUPPORT AND PROTECTIVE COLLAR

(71) Applicant: SCALPAL LLC, Wilmington, DE (US)

(72) Inventors: Eliot Robert Gitman, Jerusalem (IL); Tuvia Gitman, Jerusalem (IL)

(73) Assignee: SCALPAL LLC, Wilmington, DE (US)

( * ) Notice: Subject to any disclaimer, the term of this patent is extended or adjusted under 35 U.S.C. 154(b) by 1238 days.

(21) Appl. No.: 14/939,150

(22) Filed: Nov. 12, 2015

(65) Prior Publication Data

US 2017/0135901 A1    May 18, 2017

(51) Int. Cl.
  *A61J 1/16*     (2006.01)
  *A61J 1/20*     (2006.01)
  (Continued)

(52) U.S. Cl.
  CPC .............. *A61J 1/16* (2013.01); *A61J 1/2055* (2015.05); *A61J 1/2096* (2013.01);
  (Continued)

(58) Field of Classification Search
  CPC .......... A61J 1/16; A61J 1/2096; A61J 1/1425; A61J 1/1493; A61J 1/2055; A61J 1/2089; A61M 5/1782; A61M 5/321; A61M 2005/2492; F16L 55/035; F16L 55/0335; F16L 3/1211; F16L 3/10; F16L 3/105; F16L 3/1058; A47G 23/03; A47G 19/2261; A47G 23/0216; A47G 23/0241; A47G 29/093; B65D 23/001; B65D 23/0885; B65D 25/24; B65D 81/3876; B65D 2303/00; B65D 25/20; B65D 77/0493; B65D 23/0871; B01L 9/06; B01L 2300/123; F16F 1/3732; A47L 9/22; H02K 5/24; B67C 3/24; F16M 11/04
  (Continued)

(56) References Cited

U.S. PATENT DOCUMENTS 1,528,713 A * 3/1925 Weirick .................. A47J 36/34
                                                     220/737
1,653,083 A * 12/1927 Blaw ....................... E04H 12/32
                                                    248/230.9
(Continued)

FOREIGN PATENT DOCUMENTS

CN           201023742 Y     2/2008
WO         2010037250 A1     4/2010
WO    WO-2013171521 A2 *    11/2013    ........... E21B 17/012

*Primary Examiner* — Muhammad Ijaz
*Assistant Examiner* — Taylor L Morris
(74) *Attorney, Agent, or Firm* — Smith, Gambrell & Russell, LLP

(57) ABSTRACT

A mount for supporting a cylindrical bottle includes an annular core having an inner side surface defining a hollow opening, an outer side surface, a top surface and a base surface. A plurality of pliable ribs each at least partially encircles the annular core so as to overlap the outer side surface, the top surface and the base surface such that at least an upper end of each rib where it overlaps the top surface extends into the hollow opening. The mount may be used in conjunction with a collar having a body portion for surrounding the bottleneck and defining along at least a portion of an axis thereof a substantially quadrilateral cross-section having in each corner thereof a respective arcuate recess.

21 Claims, 11 Drawing Sheets

(51) Int. Cl.
*A61M 5/31* (2006.01)
*A61M 5/178* (2006.01)
*A47G 23/02* (2006.01)

(52) U.S. Cl.
CPC ........ *A61M 5/3137* (2013.01); *A47G 23/0216* (2013.01); *A61M 5/1782* (2013.01); *A61M 2005/3139* (2013.01); *A61M 2209/08* (2013.01)

(58) Field of Classification Search
USPC ........... 248/74.1, 346.11, 687; 220/737, 636, 220/729, 732; 215/393; 267/140.12
See application file for complete search history.

(56) References Cited

U.S. PATENT DOCUMENTS

| | | | | |
|---|---|---|---|---|
| 2,086,674 | A * | 7/1937 | Lodin | B67B 7/186 81/3.32 |
| 2,122,722 | A * | 7/1938 | O'Neill | A61M 5/00 604/414 |
| 2,189,587 | A * | 2/1940 | Lallement | B08B 9/423 198/803.15 |
| 2,215,283 | A * | 9/1940 | Adler | F16L 3/1233 138/107 |
| 2,563,698 | A * | 8/1951 | Whitebread | A47G 29/093 24/457 |
| 2,634,940 | A * | 4/1953 | Karty | B60N 3/12 248/230.9 |
| 2,727,407 | A * | 12/1955 | Richards | F16B 39/24 74/575 |
| 2,782,614 | A * | 2/1957 | Currie | B65D 25/20 220/718 |
| 2,814,267 | A * | 11/1957 | Goldstein | A47G 23/0306 116/309 |
| 2,853,261 | A * | 9/1958 | Loeb | A47G 23/0216 248/151 |
| 3,096,960 | A * | 7/1963 | Kinney | A47L 13/512 248/113 |
| 3,284,037 | A * | 11/1966 | Muller | F16L 3/133 248/60 |
| 3,302,915 | A * | 2/1967 | Usher | F16L 3/123 248/74.3 |
| 3,327,893 | A * | 6/1967 | Graves | B65D 25/24 19/159 R |
| 3,345,245 | A * | 10/1967 | Hanusa | B32B 27/00 138/111 |
| 3,434,682 | A * | 3/1969 | Nestlerode, Sr. | E21B 17/1035 248/68.1 |
| 3,606,218 | A * | 9/1971 | Enlund | F16L 3/1091 248/74.2 |
| 3,762,673 | A * | 10/1973 | Koslovsky | A61J 1/16 108/26 |
| 3,875,979 | A * | 4/1975 | Hults | A61M 5/1782 141/27 |
| 3,963,226 | A * | 6/1976 | Jankowski, Jr. | B65D 25/24 267/116 |
| 3,999,261 | A * | 12/1976 | Bingaman | A47G 23/02 269/217 |
| D252,441 | S * | 7/1979 | Allen | D34/6 |
| 4,189,807 | A * | 2/1980 | Byerly | F16L 3/1233 174/40 CC |
| 4,222,539 | A * | 9/1980 | Kramer | F16L 3/123 248/74.3 |
| 4,367,572 | A * | 1/1983 | Zielenski | B60R 16/04 180/68.5 |
| 4,441,677 | A * | 4/1984 | Byerly | F16L 3/1233 24/16 PB |
| 4,595,515 | A * | 6/1986 | Wakino | F16F 1/3605 252/500 |
| 4,675,020 | A * | 6/1987 | McPhee | A61J 1/2089 604/411 |
| 4,713,900 | A * | 12/1987 | Calloway, Jr. | G09F 3/00 40/310 |
| 4,746,017 | A * | 5/1988 | Howard | B65D 11/04 206/438 |
| 4,880,130 | A * | 11/1989 | Blake | B65D 25/20 220/655 |
| 4,969,618 | A * | 11/1990 | Thompson | A47G 7/025 248/152 |
| 5,000,331 | A * | 3/1991 | Conlon | B01L 9/00 215/12.1 |
| 5,098,051 | A * | 3/1992 | Aldridge | G09F 7/18 248/219.4 |
| 5,123,558 | A * | 6/1992 | Moloney | A47G 23/03 220/212 |
| 5,180,132 | A * | 1/1993 | Pearson | A47G 23/0225 248/205.5 |
| 5,222,701 | A * | 6/1993 | Rowland | B65H 75/366 248/222.13 |
| 5,279,576 | A * | 1/1994 | Loo | A61J 1/2096 222/1 |
| 5,356,406 | A * | 10/1994 | Schraga | A61J 1/2096 215/DIG. 3 |
| 5,385,555 | A * | 1/1995 | Hausser | A61M 5/3243 604/110 |
| 5,390,795 | A * | 2/1995 | Jobmann | B65D 21/0201 206/515 |
| 5,433,324 | A * | 7/1995 | Leonard | A61J 7/04 206/446 |
| 5,447,764 | A * | 9/1995 | Langford | A47G 23/0216 220/560 |
| 5,590,782 | A * | 1/1997 | Haber | A61J 1/16 206/528 |
| 5,592,975 | A * | 1/1997 | Wissmann | F16L 7/00 138/112 |
| 5,647,845 | A * | 7/1997 | Haber | A61J 1/10 604/32 |
| 5,660,138 | A * | 8/1997 | Hirsch | A61J 7/04 116/308 |
| 5,664,753 | A * | 9/1997 | Takei | A47G 23/0241 248/146 |
| 5,692,640 | A * | 12/1997 | Caulfield | G06F 19/3468 221/199 |
| 5,732,915 | A * | 3/1998 | Heard | G09F 7/18 248/218.4 |
| 5,738,334 | A * | 4/1998 | Proni | A61M 39/045 251/149.1 |
| 5,776,124 | A * | 7/1998 | Wald | A61J 1/2096 604/403 |
| 5,797,897 | A * | 8/1998 | Jepson | A61J 1/2089 604/239 |
| 5,803,285 | A * | 9/1998 | Hirota | B65D 39/16 215/296 |
| 5,813,638 | A * | 9/1998 | Morris | A47G 19/08 220/574 |
| 5,857,579 | A * | 1/1999 | Finneran | B65D 1/0246 215/252 |
| 5,897,090 | A * | 4/1999 | Smith | B01L 9/06 206/306 |
| 5,944,700 | A * | 8/1999 | Nguyen | A61M 5/46 604/117 |
| 5,961,086 | A * | 10/1999 | Moore | B01L 9/06 248/314 |
| 5,985,219 | A * | 11/1999 | Lind | B01L 9/06 422/562 |
| 6,109,577 | A * | 8/2000 | Dziedzic | G09F 7/18 248/230.8 |
| 6,152,185 | A * | 11/2000 | Tucker | F16L 11/12 138/103 |
| 6,205,888 | B1 * | 3/2001 | Laudani | B67B 7/18 269/254 R |
| 6,240,668 | B1 * | 6/2001 | Clawson | G09F 3/00 40/306 |
| 6,247,686 | B1 * | 6/2001 | Gabbin | F16F 1/3732 267/147 |
| 6,253,804 | B1 * | 7/2001 | Safabash | A61J 1/2096 141/311 R |

(56) References Cited

U.S. PATENT DOCUMENTS

| | | | | |
|---|---|---|---|---|
| 6,286,798 B1* | 9/2001 | Chun | A47G 23/0216 | 206/218 |
| 6,443,403 B1* | 9/2002 | Page | F16L 3/1233 | 24/16 PB |
| 6,565,054 B2* | 5/2003 | Weesner | A61M 5/008 | 248/229.17 |
| 6,578,809 B1* | 6/2003 | Dimella | A47G 23/032 | 248/346.11 |
| 6,594,928 B1* | 7/2003 | Clawson | B65D 25/20 | 215/365 |
| 6,612,526 B2* | 9/2003 | Meuth | E21B 17/012 | 24/68 R |
| 6,971,506 B2* | 12/2005 | Hassinen | G01N 35/04 | 198/803.14 |
| 6,988,824 B2* | 1/2006 | Santospago | B01F 11/0008 | 220/737 |
| 7,055,224 B2* | 6/2006 | Bathey | B65F 1/06 | 24/30.5 R |
| 7,059,368 B2* | 6/2006 | Filler | A61J 1/2096 | 141/27 |
| 7,077,176 B2* | 7/2006 | Py | A61J 1/18 | 141/301 |
| 7,122,158 B2* | 10/2006 | Itoh | B01L 9/06 | 422/562 |
| 7,216,837 B2* | 5/2007 | Pineda | A47G 7/025 | 248/104 |
| 7,243,894 B2* | 7/2007 | Haregoppa | B06B 3/00 | 248/638 |
| 7,264,121 B2* | 9/2007 | Ishikawa | B67C 3/24 | 206/583 |
| 7,328,876 B2* | 2/2008 | Jones | B60N 3/107 | 220/694.1 |
| 7,331,707 B2* | 2/2008 | DelValle | A44C 5/0015 | 116/308 |
| 7,387,049 B1* | 6/2008 | Ver Hage | A01K 7/00 | 53/490 |
| 7,422,181 B2* | 9/2008 | Sußenbach | F16L 3/10 | 174/664 |
| 7,537,136 B2* | 5/2009 | Hechmati | A47G 23/0216 | 220/737 |
| 7,726,621 B1* | 6/2010 | Dellinger | B44D 3/14 | 220/737 |
| 7,731,144 B2* | 6/2010 | Kazyaka | B60N 3/107 | 248/311.2 |
| 7,748,293 B2* | 7/2010 | Elwell | B67B 7/18 | 7/151 |
| 7,845,505 B2* | 12/2010 | Hamamoto | B65D 39/16 | 215/249 |
| 7,926,780 B2* | 4/2011 | Yeh | F16F 15/08 | 248/632 |
| 8,028,850 B2* | 10/2011 | Zimmerman | A47G 19/2261 | 220/23.89 |
| 8,087,528 B1* | 1/2012 | Scarlett | A47G 23/0216 | 220/23.89 |
| 8,215,593 B2* | 7/2012 | Van Walraven | F16L 55/035 | 248/60 |
| 8,220,629 B2* | 7/2012 | Crosby | A45D 40/265 | 116/309 |
| 8,225,949 B2* | 7/2012 | Aneas | B65D 51/002 | 215/249 |
| 8,381,361 B2* | 2/2013 | Serna-Gongora | F16L 3/133 | 24/20 R |
| 8,475,404 B2* | 7/2013 | Foshee | A61J 1/2096 | 604/82 |
| 8,512,295 B2* | 8/2013 | Evans | A61M 5/3202 | 215/216 |
| 8,662,580 B2* | 3/2014 | Henke | B60N 3/101 | 297/188.14 |
| 8,672,176 B2* | 3/2014 | Sayasithsena | A47G 23/0216 | 220/4.01 |
| 8,684,624 B2* | 4/2014 | Slayne | F16D 1/0835 | 403/365 |
| 8,733,724 B2* | 5/2014 | Voigt | B60N 3/101 | 220/703 |
| 8,833,707 B2* | 9/2014 | Steinberg | A61G 13/102 | 128/849 |
| 8,870,132 B2* | 10/2014 | Sampson | F16L 3/123 | 248/62 |
| 8,876,367 B1* | 11/2014 | Howe | B01F 11/0008 | 248/316.2 |
| 9,133,006 B2* | 9/2015 | Kelley | B67C 7/00 | |
| 9,211,543 B2* | 12/2015 | Ohga | B01L 9/06 | |
| 9,290,302 B2* | 3/2016 | Horn | A61J 7/0481 | |
| 9,428,969 B2* | 8/2016 | Harbison | E21B 17/012 | |
| 9,844,846 B2* | 12/2017 | Terzini | B23Q 1/032 | |
| 9,855,193 B2* | 1/2018 | O'Doherty | A61J 7/04 | |
| D827,153 S * | 8/2018 | Bantug | D24/227 | |
| 2002/0117587 A1* | 8/2002 | Tenma | F16L 3/105 | 248/49 |
| 2004/0129596 A1* | 7/2004 | Geert | A61J 1/16 | 206/521 |
| 2004/0205938 A1* | 10/2004 | Blauer | A45C 13/26 | 16/431 |
| 2005/0205752 A1* | 9/2005 | Pauli | B65D 23/001 | 248/680 |
| 2006/0060592 A1* | 3/2006 | Kamite | B65D 23/0885 | 220/737 |
| 2006/0118507 A1* | 6/2006 | Feldman | B65D 23/0871 | 215/12.1 |
| 2007/0079894 A1* | 4/2007 | Kraus | A61M 5/32 | 141/319 |
| 2007/0080593 A1* | 4/2007 | O'Donnell | H02K 5/1672 | 310/90 |
| 2007/0108205 A1* | 5/2007 | Porras | A61J 1/1412 | 220/23.87 |
| 2007/0214692 A1* | 9/2007 | Ferrara | A61J 1/2096 | 40/324 |
| 2008/0011925 A1* | 1/2008 | Ruff | B60N 3/103 | 248/310 |
| 2008/0065024 A1* | 3/2008 | Witte | A61M 5/1782 | 604/191 |
| 2008/0105584 A1* | 5/2008 | Cecil | B65D 21/0224 | 206/516 |
| 2008/0179353 A1 | 7/2008 | Maymon | | |
| 2008/0312634 A1* | 12/2008 | Helmerson | A61J 1/2096 | 604/414 |
| 2009/0095865 A1* | 4/2009 | Everhart | B60N 3/105 | 248/309.1 |
| 2010/0038273 A1* | 2/2010 | Johnson | B65D 23/0885 | 206/459.5 |
| 2010/0140431 A1 | 6/2010 | Van Horne | | |
| 2010/0213206 A1* | 8/2010 | Greene | A47G 23/0216 | 220/752 |
| 2011/0061424 A1* | 3/2011 | Gupta | A44C 5/0015 | 63/1.13 |
| 2011/0108513 A1* | 5/2011 | Peter | B65D 21/0204 | 215/376 |
| 2011/0140412 A1* | 6/2011 | Manser | F17C 13/084 | 285/192 |
| 2012/0000570 A1* | 1/2012 | Foscarota | A61J 1/16 | 141/2 |
| 2012/0065611 A1* | 3/2012 | Musani | A61M 5/1782 | 604/415 |
| 2012/0091296 A1* | 4/2012 | Lee | A47G 23/0216 | 248/122.1 |
| 2012/0211503 A1* | 8/2012 | LaFaver | B65D 23/0871 | 220/676 |
| 2012/0241332 A1 | 9/2012 | Crossman | | |
| 2013/0098930 A1* | 4/2013 | Ong | A47J 45/10 | 220/694 |
| 2013/0206783 A1* | 8/2013 | Hecht | B01L 9/06 | 220/737 |
| 2013/0240476 A1* | 9/2013 | Aneas | B65D 51/002 | 215/320 |
| 2013/0303994 A1* | 11/2013 | Gaillot | A61J 1/2096 | 604/239 |
| 2014/0008319 A1* | 1/2014 | Buxton-Dakides | A61J 1/03 | 215/230 |

(56) References Cited

U.S. PATENT DOCUMENTS

| | | | | |
|---|---|---|---|---|
| 2014/0097323 A1* | 4/2014 | Lamb | A47L 9/22 | 248/634 |
| 2014/0166838 A1* | 6/2014 | Murray | B01F 15/00772 | 248/346.03 |
| 2014/0173856 A1* | 6/2014 | Kingston | F16L 1/24 | 24/285 |
| 2014/0231439 A1* | 8/2014 | Manser | F16M 11/04 | 220/581 |
| 2014/0290792 A1* | 10/2014 | Avery | A61M 5/24 | 141/18 |
| 2014/0339387 A1* | 11/2014 | Bolze | H01Q 1/1221 | 248/237 |
| 2014/0353337 A1* | 12/2014 | Suzuki | A61J 1/067 | 222/183 |
| 2015/0101706 A1* | 4/2015 | Fukuoka | A61J 1/2096 | 141/27 |
| 2015/0290079 A1* | 10/2015 | Nishioka | A61J 1/1406 | 604/408 |
| 2015/0297451 A1* | 10/2015 | Marici | A61J 1/2055 | 604/403 |
| 2016/0207678 A1* | 7/2016 | Tuan | A47B 97/00 | |
| 2016/0278557 A1* | 9/2016 | Esposito | A47G 23/0225 | |
| 2016/0318659 A1* | 11/2016 | Luna | B65D 25/34 | |
| 2016/0367439 A1* | 12/2016 | Davis | A61J 1/2096 | |
| 2017/0027358 A1* | 2/2017 | Weissbart | A47G 23/03 | |
| 2017/0204992 A1* | 7/2017 | Kingston | F16L 1/24 | |
| 2017/0225849 A1* | 8/2017 | Miros | A45F 3/18 | |
| 2017/0231869 A1* | 8/2017 | Zerebny | A61J 1/16 | 248/206.2 |
| 2017/0273485 A1* | 9/2017 | Rao | B65D 81/3806 | |

* cited by examiner

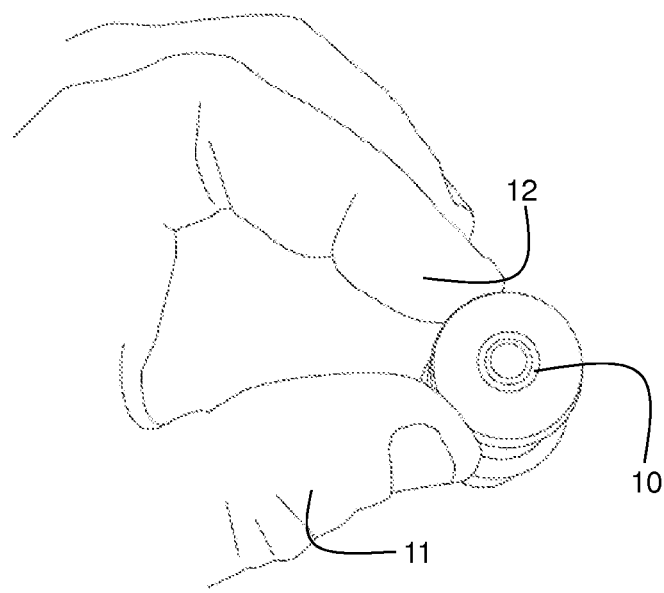
Fig. 1a
(Prior Art)
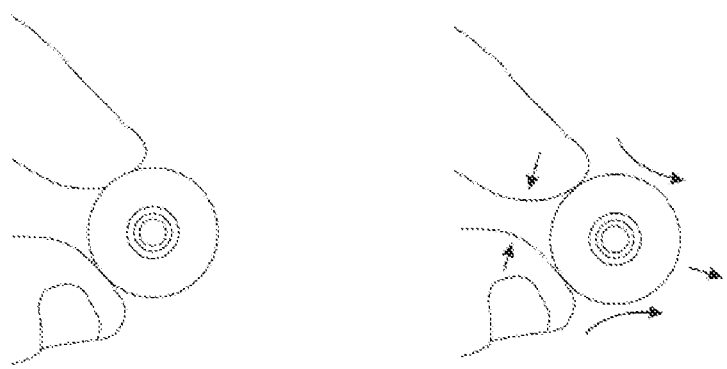
Fig. 1b
(Prior Art)
Fig. 1c
(Prior Art)
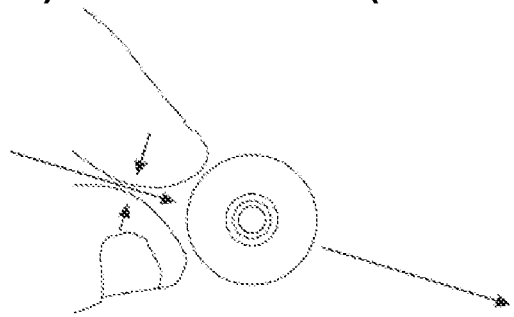
Fig. 1d
(Prior Art)

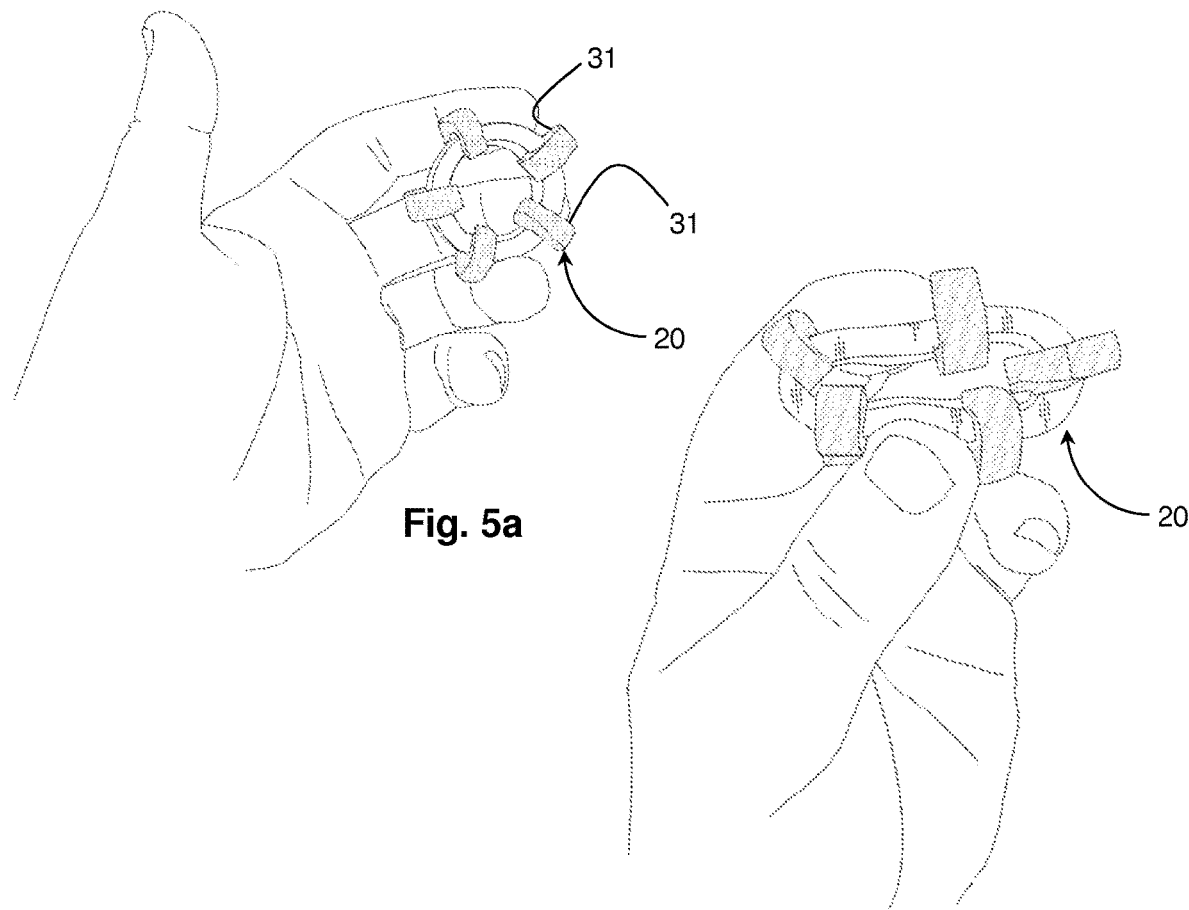
Fig. 5a
Fig. 5b
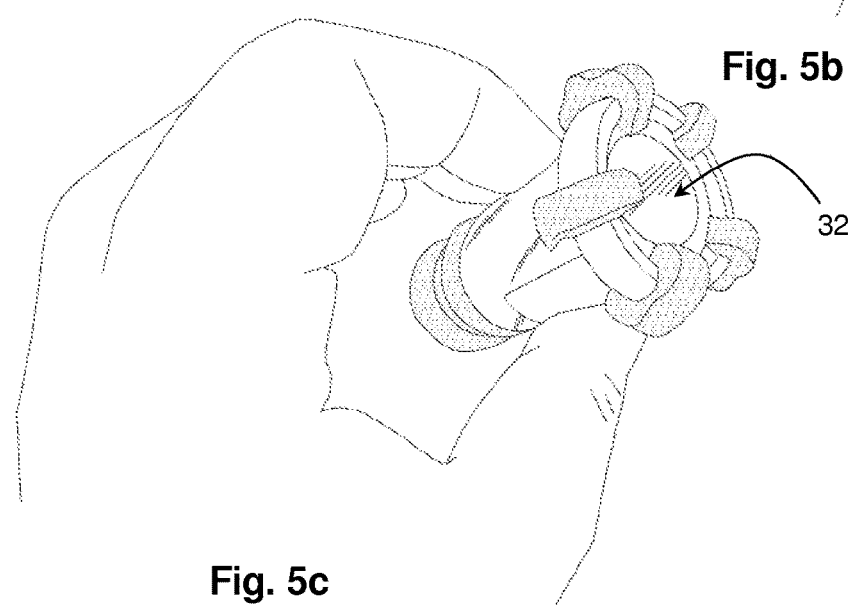
Fig. 5c

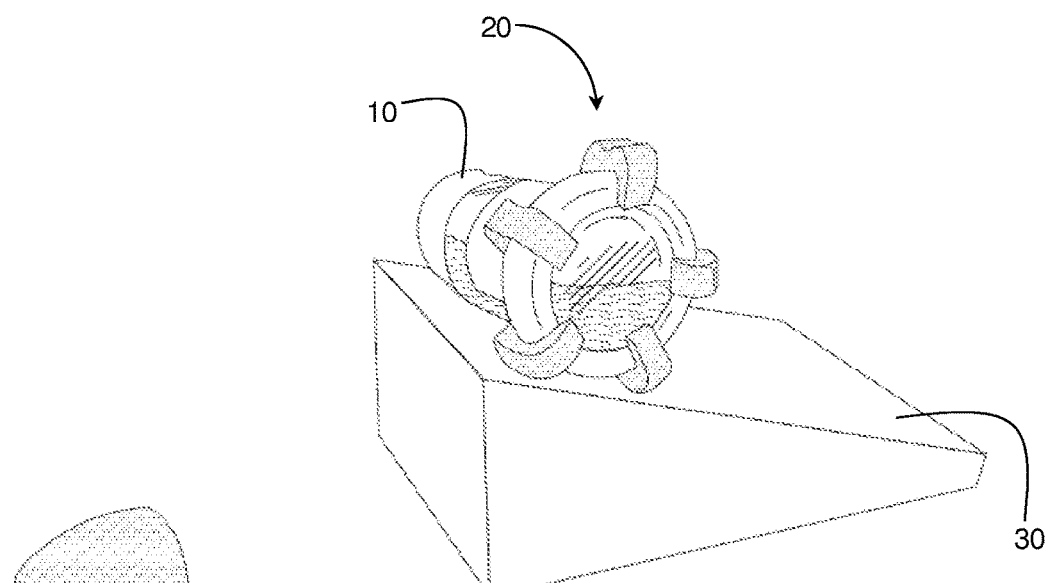
Fig. 6a
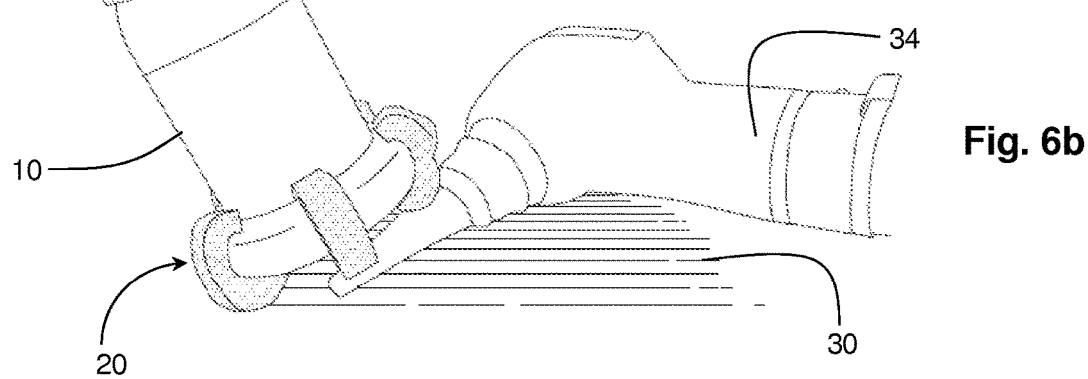
Fig. 6b
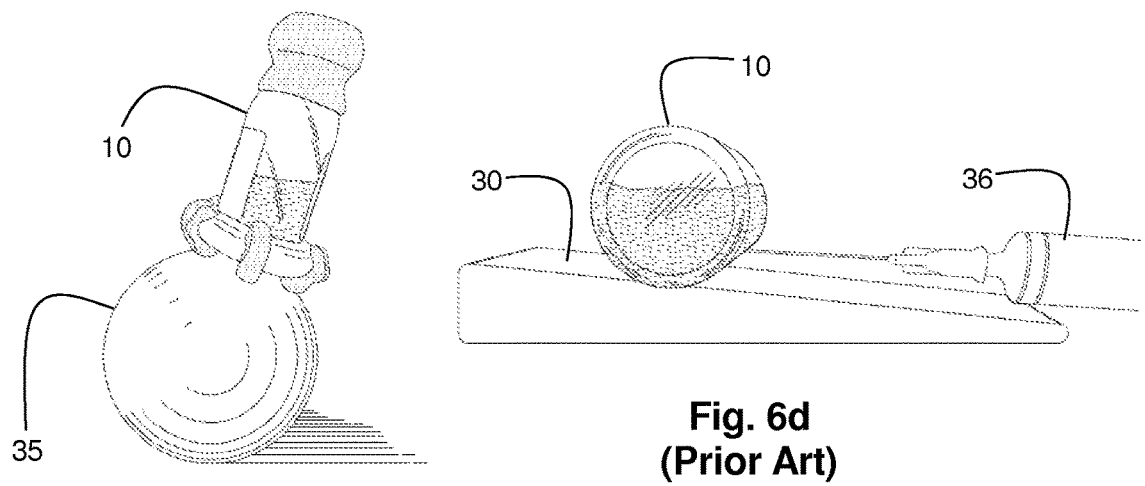
Fig. 6c
Fig. 6d (Prior Art)

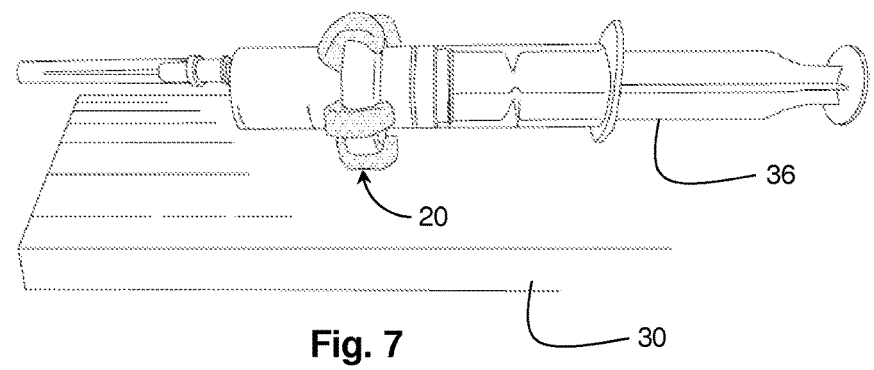
Fig. 7
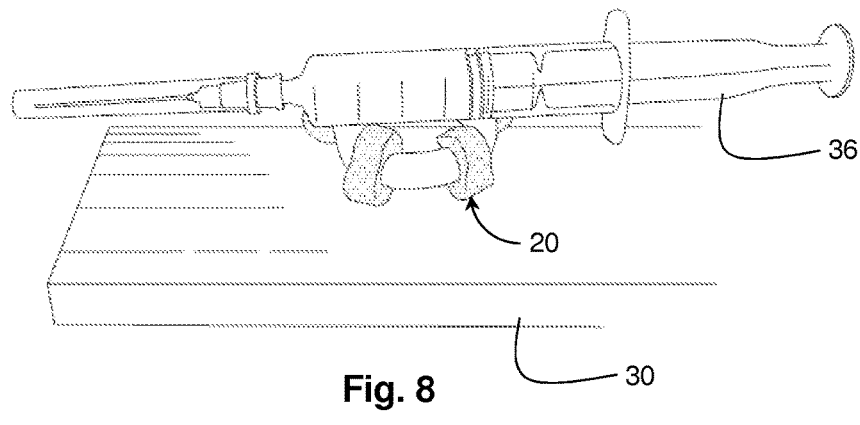
Fig. 8
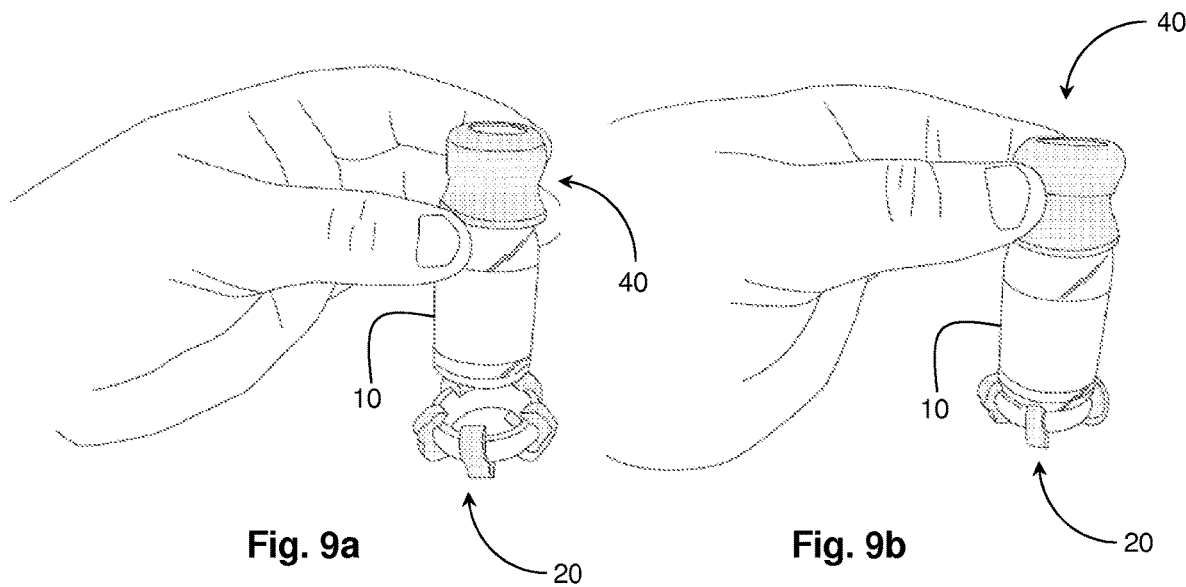
Fig. 9a Fig. 9b

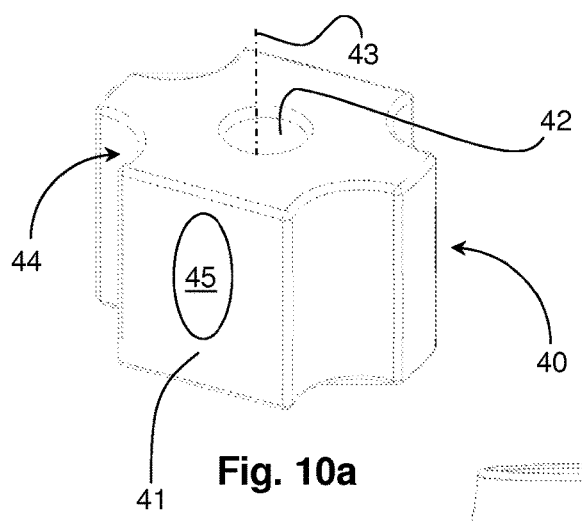
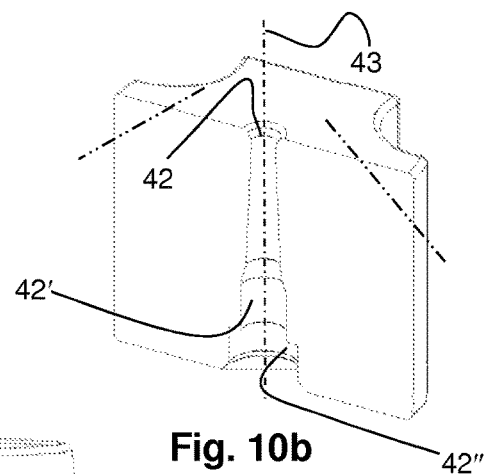
Fig. 10a
Fig. 10b
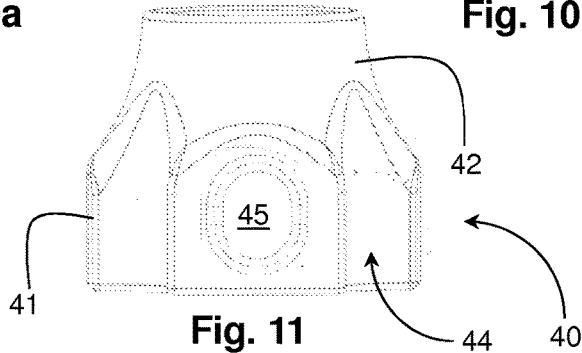
Fig. 11
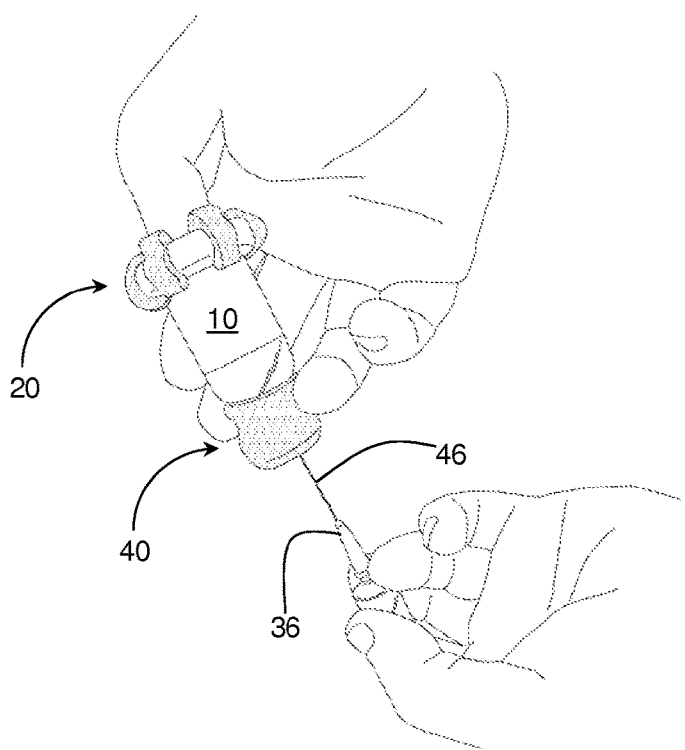
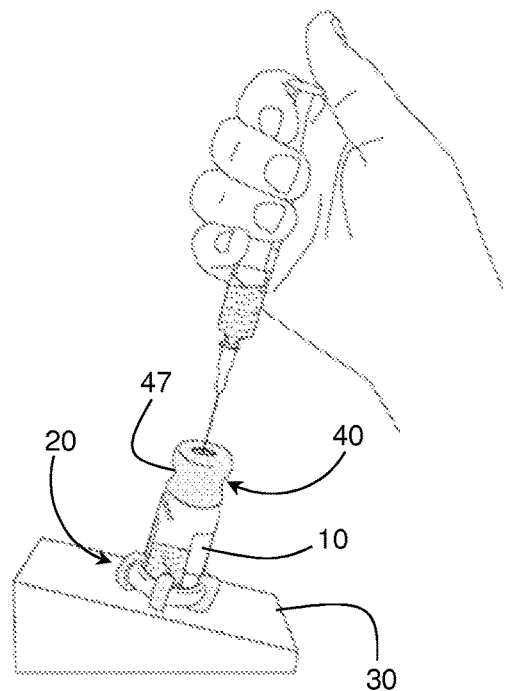
Fig. 12
Fig. 13

BOTTLE SUPPORT AND PROTECTIVE COLLAR

FIELD OF THE INVENTION

This invention relates to a support element for bottles.

BACKGROUND OF THE INVENTION

Bottles are inherently unstable owing to their cylindrical geometry, which renders them prone to slip and roll. Likewise, if inadvertently tilted, they are apt to tip and spill their contents if open or insufficiently sealed. This is at best a nuisance but can be hazardous if the contents are chemicals or medicines. There are many different types of bottle supports, some of which are intended to address these issues.

US 2012/0241332 discloses a multipack carrier for bottles, cans, or jars having a plurality of plastic braces each comprising a circular cutout for accommodating the neck of the bottle and a plurality of internal webs in the plane of the cutout that are flexed and resiliently grasped by the bottle neck. The device is used to carry multiple bottles but does not support them from falling or tipping over when disposed on a flat surface.

US 2010/0140431 discloses a bottle support comprising a cylindrical ring and a plurality of internal webs mounted parallel to an axis of the ring and each fixed to an inside surface thereof. The webs are flexed radially and resiliently grasped by the bottle neck for supporting an inverted container on a flat surface. Although this device will support a bottle disposed on a flat surface, it requires that all the webs are flexed equally and this militates against supporting a bottle at an angle.

In addition to the need to support bottles of different sizes on a flat surface, there is also a need to lift and hold bottles securely. FIGS. 1a, 1b, 1c and 1d show pictorially the tendency for round and cylindrical objects 10 to slip when grasped between thumb 11 and forefinger 12. When a gripping force is applied as shown in FIG. 1c between points on the side surfaces of a cylindrical object 10 that are not diametrically opposite each other, a component of the gripping force acts to push the object out of the user's grip. This tendency is increased if friction between the user's fingers and the outer surface of the object is reduced, such as when a bottle is gripped with wet or soapy hands. This tendency to slip from the user's grip is equally true for bottle supports of the type described in above-mentioned US 2010/0140431 owing to the smooth side surface of the cylindrical ring.

FIGS. 2a and 2b show pictorially a bottle 10 gripped non-diametrically between the thumb 11 and forefinger 12 of a user's hand. If the segment that is closer to the center 13 of the oblique arch between thumb and forefinger and bound by the points at which the bottle is gripped has an area less than half that of the bottle's cross-section, the gripping force will have a tangential component that urges the bottle away from the center 13 of the oblique arch. The bottle 10 will then slip out of the user's hand. Conversely, if the area of this segment is greater than half that of the bottle's cross-section, the gripping force will have a tangential component that urges the bottle toward the center 13 of the oblique arch into the user's hand. In either case, the transverse grip on the bottle will be lost and the bottle will slip.

The need to support bottles stably becomes all the more urgent when the bottles contain medicines and other liquid contents that are required to be removed or injected. For example, liquid medicine bottles are often provided with a resealable cap through which a hypodermic needle is inserted in order to withdraw a quantity of liquid. Alternatively, liquid in a hypodermic syringe may need to be injected into a vial or other container. Both of these operations require that the via or bottle be retained securely on a support surface, possibly inclined to the horizontal, in order to provide direct access to the cap and ensure visual alignment thereof to the tip of the hypodermic needle.

There is therefore a need for a device that allows the bottle to be disposed stably on a support surface while allowing it to be gripped securely and reliably without the associated risk of slippage, particularly when gripped using wet hands.

In addition to the problem of rolling and tilting of bottles and the like, there is another and in some respects associated problem of handling bottles securely when filling them or extracting liquids therefrom. This problem may at first seem quite dissociated from the stability issues that we have raised above, but frequently the very act of injecting liquid into a bottle or extracting liquid therefrom is what induces instability in the first place.

Thus, liquids may be extracted from bottles such as medicine vials or injected therein in one of two ways, which we will describe with reference to a typical medical scenario. In one way, the bottle is placed on a work surface and the needle of a hypodermic syringe is inserted into the neck of the bottle. Provided that the only force applied is vertical, this should avoid any tendency to skid. But in practice, this is difficult to achieve. Medical orderlies work under pressure and work surfaces are often wet, so that any slight displacement of the needle from the vertical induces a horizontal force component that causes the bottle to slip. Alternatively, the bottle is gripped in one hand by or toward the neck and the hypodermic syringe is operated with the other hand. Not infrequently this is done with wet hands or gloves and this causes the bottle or vial to slip from the user's grip in the same manner as explained above with reference to FIGS. 1 and 2 of the drawings. Furthermore, this technique requires axial alignment between the tip of the needle and the neck of the bottle. Under stress it is all too easy to miss the bottle and the exposed fingers of the user's other hand are then at risk of being pricked and possibly injected with the contents of the hypodermic syringe.

The tendency of bottles to slip from a user's grip has been addressed in the art. For example, CN 2010/23742 discloses a bottle sheath disposed between the neck and the middle portion of a bottle and fixed to the bottle body. WO 2010/037250 discloses a non-slip sleeve that is removably fitted around the neck of a bottle. US 2008/0179353 discloses a sleeve that is secured around the neck of a wine bottle for preventing dripping when pouring.

None of these references discloses a non-slip sheath that may be removably attached to the neck of a bottle and is configured to coupling to a hypodermic syringe.

The invention also addresses a number of problems associated with hypodermic syringes. First, the sharp needle is a common source of injury to both patient and medical staff. Initially the needle is protected by a guard, which must be removed prior to use often under conditions that may be stressful for the patient. A patient who wriggles increases the risk that the medical orderly will inject the needle poorly, thus causing hardship to the patient; and will more easily render the medical orderly prone to self-injury. Hypodermic needles are typically injected into a blood vessel at an acute angle to the surface of the skin of about 15° or vertically at 90°, although they may be injected at other angles. The manner of use typically requires use of both hands as shown in FIG. 2c. Alternatively, one hand may be used to hold the syringe and manipulate the plunger while a finger of the other hand is placed under the body of the syringe and serves as a fulcrum or pivot point that allows the medical orderly to guide the syringe at the appropriate angle with more control than could be achieved using only one hand. In either case, the close proximity of the other hand to the syringe renders it subject to self-injury, particularly if the patient moves unexpectedly.

Further problems relate to the extent to which the needle projects from the end of the syringe. Generally, the length of the needle determines the maximal depth of penetration, which itself is a function of the medical procedure. In other words, some procedures may require only superficial penetration while others may require that the needle be injected to a depth of over one-inch i.e. more than 2.5 cm. The longer the needle, the higher is the risk of injury and the more frightening it is to the patient. This is why patient management often dictates that the needle guard be removed out of sight of the patient and that the needle not be brandished in the sight of the patient. But regardless of when the needle guard is removed, the needle must be exposed prior to use and it is during this exposure that the medical orderly is most at risk of self-injury.

Another common source of injury occurs when lifting a hypodermic syringe from a supine position. During medical procedures, a nurse typically hands the surgeon a tray on which there are disposed multiple instruments for carrying out the procedure and from which the surgeon selects the appropriate instrument. The hands of the surgeon may be wet and a hypodermic syringe being cylindrical can easily slip from the surgeon's grip. It should be borne in mind that optimal gripping is always achieved by the arch between thumb and forefinger, as explained above with reference to FIG. 2a. This is how screwdrivers, for example, are gripped in a manner that allows adequate torque to be applied. However, hypodermic syringes are not amenable to be grasped in this manner and in practice a medical orderly is constrained to lift them using only his or her finger tips, thus vastly increasing the likelihood of slippage and self-injury.

SUMMARY OF THE INVENTION

One object of the present invention is to provide an improved bottle support that allows bottles to be supported by either their base or their neck and to be retained in the bottle support at an angle without detracting from the stability of the support.

Another object is to address and alleviate some of the aforementioned problems relating to safe transfer of liquid from a bottle to another container, particularly albeit not only to hypodermic syringes.

Yet a further object is to address and alleviate some of the aforementioned problems relating to use of hypodermic syringes.

To this end there is provided in accordance with the invention a bottle support and a collar having the features of the respective independent claims.

In some embodiments the bottle support comprises:

an annular core having an inner side surface defining a hollow opening, an outer side surface, a top surface and a base surface, and a plurality of pliable ribs each at least partially encircling the annular core so as to overlap the base surface, the top surface and the outer side surface such that at least an upper end of each rib where it overlaps the top surface extends into the hollow opening.

The ribs are mounted parallel to a longitudinal axis of the core but unlike the arrangement in US 2010/0140431 they cover at least partially the outer surface and project over the top surface. Furthermore, they extend into the hollow opening so as to be resiliently deformed by a bottle inserted therein and thereby grasp the bottle.

In some embodiments, the lower ends of the ribs extend into the hollow opening so as to provide a platform for supporting the base of the bottle and ensuring that it does not make direct contact with a surface on which the bottle support is disposed. This prevents contamination reaching a sterile bottle.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1a to 1d show schematically the tendency of a cylindrical bottle to slip when gripped non-diametrically;

FIGS. 4a and 4b show pictorially a cylindrical bottle supported within the bottle support of FIG. 3a;

FIGS. 5a, 5b and 5c show pictorially the bottle support securely held between thumb and forefinger;

FIGS. 6a, 6b and 6c show pictorially the bottle support preventing rolling or tipping of an inclined bottle;

FIG. 6d shows how a cylindrical bottle may be prevented from rolling without use of the bottle support according to the invention;

FIG. 7 shows pictorially use of the bottle support to avoid rolling of a hypodermic syringe;

FIG. 8 shows pictorially use of the bottle support to isolate a hypodermic syringe from a working surface;

FIGS. 9a and 9b show pictorially an assembly according to a second embodiment of the invention comprising a bottle support and a collar;

FIGS. 10a and 10b show a detail of the collar according to a first embodiment;

FIG. 11 shows a detail of the collar according to a second embodiment;

FIG. 12 shows pictorially use of the collar when transferring liquid between the bottle and a hypodermic syringe;

FIGS. 13 and 14 show different uses of the bottle support to reduce the risk of self-injection or damage when transferring liquid between the bottle and a hypodermic syringe;

DETAILED DESCRIPTION OF EMBODIMENTS

In the following description of some embodiments, identical components that appear in more than one figure or that share similar functionality will be referenced by identical reference symbols.

Figure 3A:
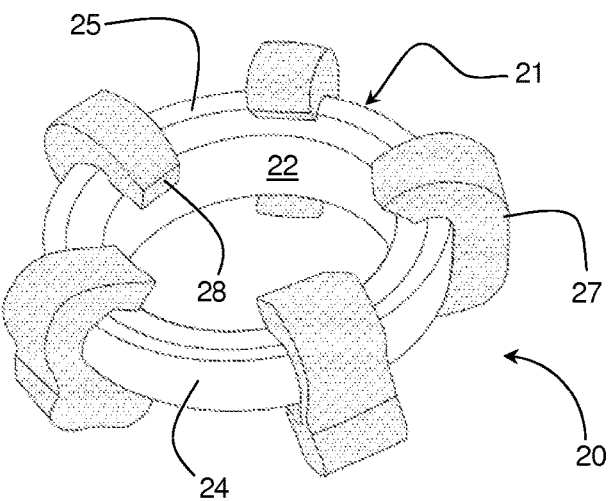
FIGS. 3a, 3b and 3c show pictorially details of a bottle support according to an embodiment of the invention.
Figure 3B:
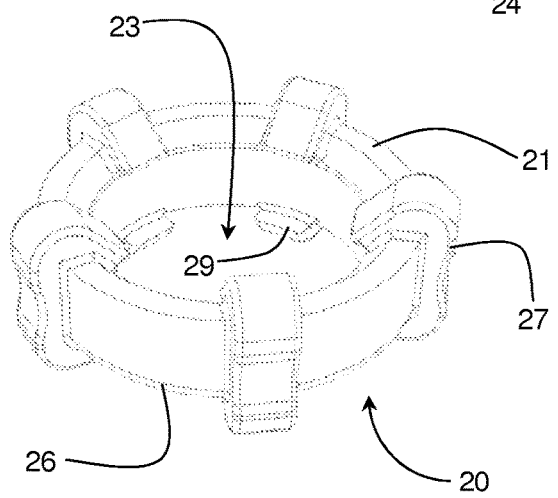
Figure 3C:
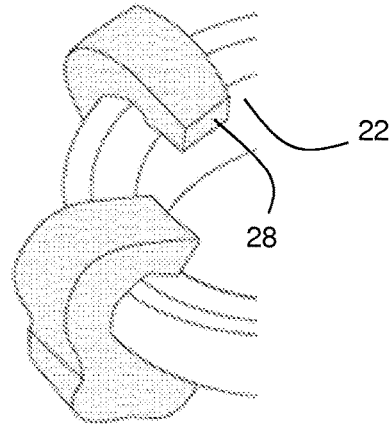

FIGS. 3a, 3b and 3c show pictorially a bottle support or mount 20 for supporting a cylindrical utensil, most typically having axial symmetry such as a cylindrical bottle. It should be noted that the bottle does not need to have a circular cross-section and the term cylindrical is used herein in its strict mathematical sense, namely a surface generated by a straight line intersecting and moving along a closed plane curve, the directrix, while remaining parallel to a fixed straight line that is not on or parallel to the plane of the directrix.

The bottle support 20 includes an annular core 21 having an inner side surface 22 defining a hollow opening 23, an outer side surface 24, a top surface 25 and a base surface 26. A plurality of pliable ribs 27 at least partially encircle the annular core 21 so as to overlap the outer side surface 24, the top surface 25 and the base surface 26 such that at least an upper end 28 of each rib where it overlaps the top surface extends into the hollow opening 23. In some embodiments the lower ends 29 of at least some of the ribs where they overlap the base surface 26 also extend into the hollow opening 23. The annular core 21 may be formed of rigid material or it may be pliable. If it is rigid and circular, then the shape of a bottle than can be conveniently inserted is largely dictated by the extent to which the ribs can deform. Typically, this will restrict use of the device to bottles of regular cross-section, most typically circular. But if the core is also formed of pliable material, then there is virtually no limit to the shape of the bottle, or any other artefact, that can be securely retained therein.

The annular core 21 and the ribs 27 may be formed of a composite molding of pliable material. Alternatively, the ribs may be a composite C-shaped molding of pliable material and may be attached to the annular core 21 using adhesive or plastic welding. In this case, there is no requirement for the annular core 21 and the ribs 27 to be formed of the same material.

Figure 2A:
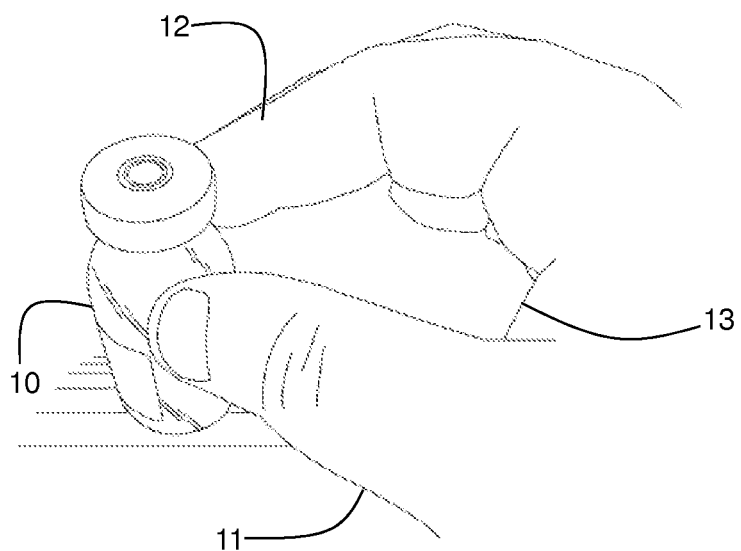
FIGS. 2a and 2b show pictorially the tendency of a cylindrical bottle to slip when gripped non-diametrically.
Figure 2B:
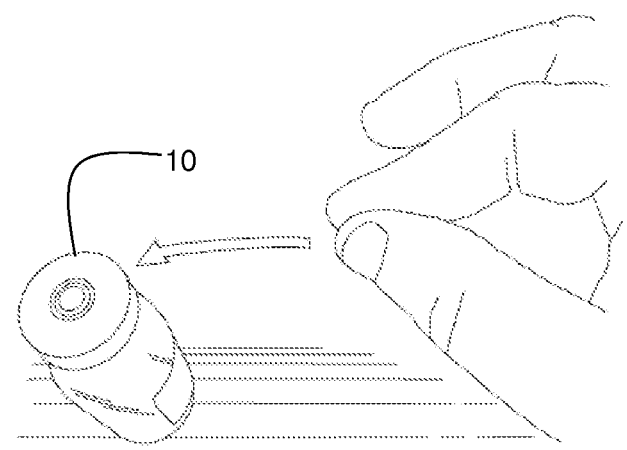
Figure 2C:
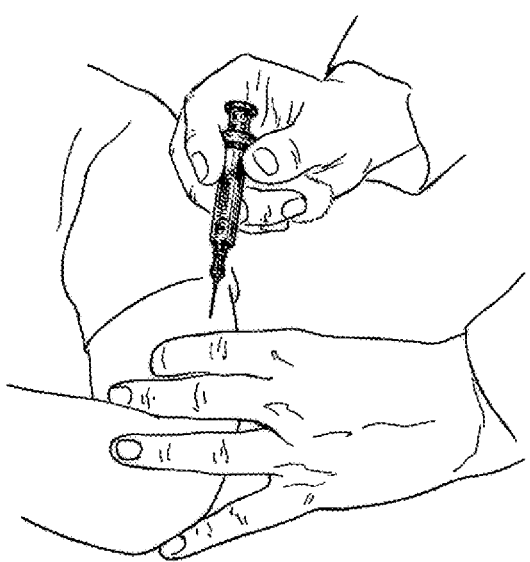
FIG. 2c shows pictorially conventional two-handed use of a hypodermic syringe.

Before describing applications of the mount, we will briefly explain the manner in which its construction is distinguished over known bottle supports. First, the pliability of the ribs 27 where they overhang the top surface 25 and extend into the hollow opening 23 allow the ribs to deform and grip the side surface of an object. Secondly, because the ribs are parallel to the axis of the core they are compressed transversely rather than deflected and no less importantly any two ribs may be deformed at different times and to different extents. This avoids the need to insert an object axially symmetrically and allows it to be inserted at an angle to axis. Thirdly, because the ribs overlap the outer side surface 24 of the core they increase the effective base area of the mount and lend added stability. Fourthly, since the ribs overlap the base surface 26, they serve to raise the base surface and insulate it from an external surface on which it is placed. Furthermore, where the lower ends of the ribs extend into the hollow opening 23, they support the base of an object supported therein and insulate it from the external surface. This helps to prevent the object, which may be a medicine bottle or vial, from becoming contaminated. Finally, because the ribs 27 extend outwardly from the generally smooth surface of the core they provide additional support surfaces that serve as ledges that are more easily grasped or pinched between thumb and forefinger or other fingers. This makes it much easier to grasp the mount securely even with wet or slippery hands and significantly reduces the tendency of the mount to roll away as shown in FIG. 2b. This functionality will now be described with reference to the drawings.

Figure 4A:
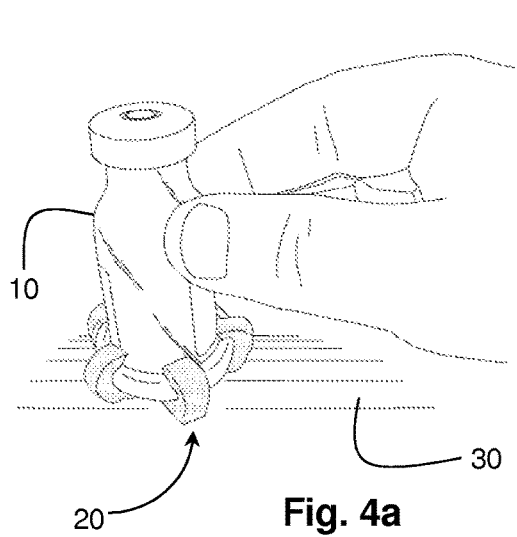
Figure 4B:
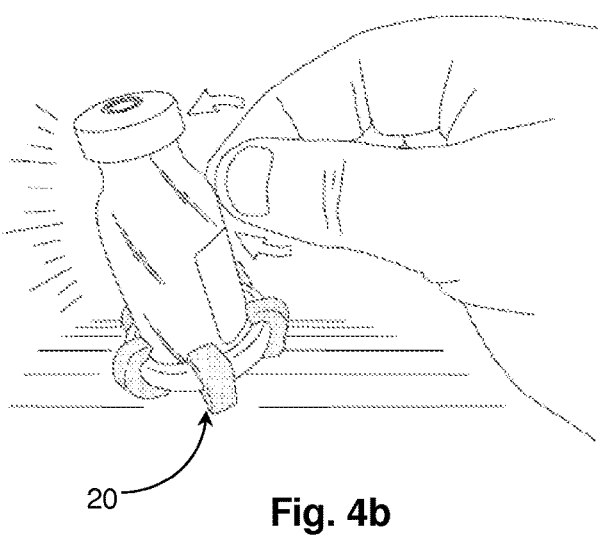

FIGS. 4a and 4b show a cylindrical bottle 10 supported by the bottle support 20. When the side surfaces of the bottle are grasped between forefinger and thumb particularly with the intention of lifting the bottle 10 from an external support surface 30, there is still a tendency for the bottle to slip away from the user's grasp. But this tendency is reduced owing to the friction between the lower surfaces of the ribs and the support surface 30.

FIGS. 5a and 5b show the bottle support securely held between the tips of two fingers or between thumb and forefinger by pinching protruding outer side surfaces 31 of the ribs that serve as ledges that are more easily grasped or pinched between the fingertips. In FIG. 5c, rather than lifting the bottle by holding the bottle support 20, the bottle 20 is grasped but with the tips of the forefinger and thumb pressing against the tops of the ribs, which likewise serve as ledges that facilitate grasped or pinched between the fingertips. It is also seen that the lower surface of the bottle does not protrude out of the lower surface of the base of the bottle holder, thus forming a recess 32 into which a user may insert his thumb or finger when grasping the bottle support from below. Applications that exploit this functionality are described below.

FIG. 6a shows the bottle support 20 preventing rolling of a bottle 10 placed on an inclined support surface 30. FIG. 6b shows that the bottle support 20 is less prone to tipping even when partially tilted owing to its being placed, possibly inadvertently, on a tool 34 lying on a level surface 30 as is easily done in stressful working conditions such as operating theaters and the like. FIG. 6c shows a bottle 10 supported within the bottle support 20 while stably retained at a significant incline on a tomato 35. FIG. 6d shows how medical staff may otherwise try to prevent a bottle 10 on an inclined surface 30 from rolling when no bottle support is available by retaining the bottle with the needle of a hypodermic syringe.

FIG. 7 shows pictorially use of the bottle support 20 to avoid rolling of a hypodermic syringe 36 by securing the bottle support 20 around the body of the syringe. Such use requires that the lower ends of the ribs of the bottle support 20 do not extend into the hollow, thus allowing the bottle support to be slid up and down the body of the syringe. FIG. 8 shows use of the bottle support 20 to isolate a hypodermic syringe 36 from a working surface 30 thus prevent cross-contamination and at the same time preventing rolling of the syringe 36. Obviously, the same principles can be applied to other utensils.

We now describe another aspect of the invention that relates to grasping a bottle not by its base but rather from its neck.

Thus, referring to FIGS. 9a and 9b there is shown a bottle 10 having attached to its neck a collar 40 for facilitating non-slip gripping of the bottle.

FIGS. 10a and 10b show a first embodiment of the collar 40 comprising a body portion 41 having an axial bore 42 for surrounding the neck of the bottle and defining along at least a portion of an axis 43 thereof a substantially quadrilateral cross-section having in each corner thereof a respective arcuate recess 44, each for accommodating a user's thumb or finger. The axial bore 42 may be configured to accommodate an end of a hypodermic syringe and, to this end, may include at least two mutually contiguous sections 42' and 42" of different cross-sectional areas so that the internal shape of the bore 42 is complementary to the external surface of the hypodermic syringe 36. The collar 40 may be formed of deformable material and dimensioned for axial compression or displacement of a predetermined distance that is adjusted to define a known protrusion of a hypodermic needle. This allows the collar 40 to be located at the end of the hypodermic needle, while concealing the tip of the needle, such that pushing the body of the syringe into the patient's skin causes the collar to compress and the needle to enter the skin. In the embodiment of FIG. 10a the body portion 41 is of rectangular cross-section and defines opposing pairs of first and second side surfaces of different widths. In other embodiments, the body portion may be of square cross-section all of whose surfaces are of equal width. At least one of the side surfaces may have an indent or depression 45 for accommodating the user's finger. By way of example, the indent may be elongated with a major axis normal to an axis of the body portion. In some embodiments the top corners of the collar may be slanted as shown schematically by chain-dotted lines in FIG. 10b so that when the collar 40 is fitted to the operative end of a hypodermic syringe as described in more detail below, the resulting slanted edges may sever to guide the insertion of the needle at an angle determined by the degree of slant.

FIG. 11 shows a second embodiment of a collar 40, having a body portion 41 an outer surface of which has a tapered portion 42 that projects axially upward opposite a base portion of the collar. The body portion includes a lower portion of substantially quadrilateral cross-section, typically square. The tapered portion 42 may be of smaller cross-sectional area than the base portion as shown in the figures so it that it tapers upward. Alternatively, it may be of larger cross-sectional area than the base portion so that it tapers downward. As in the first embodiment shown in FIG. 10a, in each corner of the body portion 41 there is formed a respective arcuate recess 44 for accommodating a user's thumb or finger. In some uses, it may be advantageous for the collar to be closed at one end to form a cap.

FIG. 12 shows use of the collar 40 when transferring liquid between the bottle 10 and a hypodermic syringe 36. Thus, the neck of the collar 40 defines a ribbed surface that is gripped between two fingers of one hand while the thumb of the same hand is held within the recess 32 of the base described above and shown in FIG. 5c. To this end, the collar may have a beveled indent 47 for better accommodating the fingers as best shown in FIG. 13. The user's other hand holds the hypodermic syringe 36 and aligns the needle 46 into the opening of the bottle. The ribbed surface of the collar 40 provides some measure of shielding that reduces the risk of self-injection.

FIG. 13 shows one use of the bottle support 20 to reduce the risk of self-injury by supporting the bottle or vial 10 in the bottle support 20 on a support surface 30 so as to obviate the need for the user to touch or hold the via while aligning the hypodermic syringe therewith.

Figure 14:
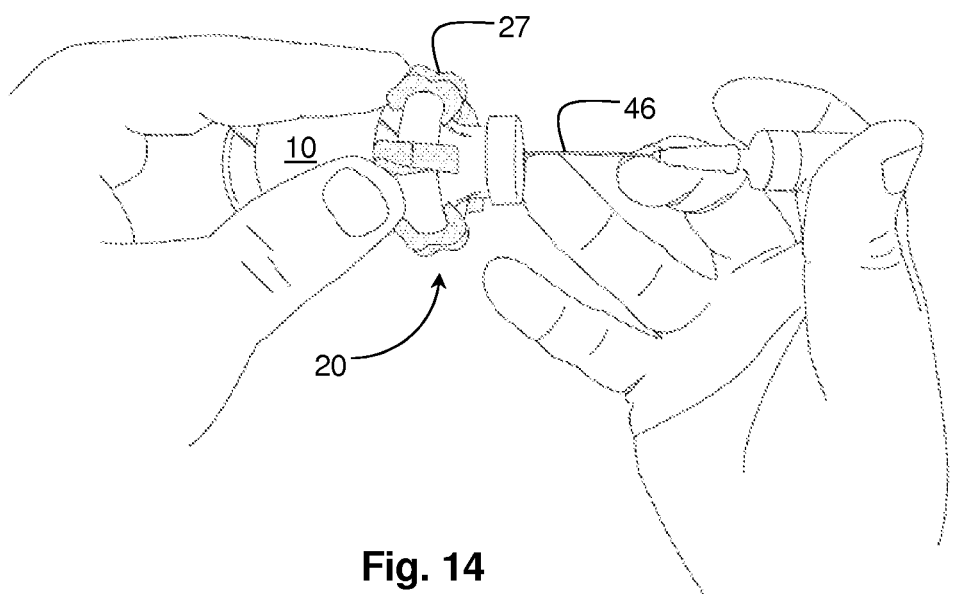

FIG. 14 shows another use of the bottle support 20 to reduce the risk of self-injury by displacing the support 20 from the base of the bottle 10 toward the neck and grasping the bottle behind the ribs 27, which completely shield the fingers from the needle 46.

Figure 15:
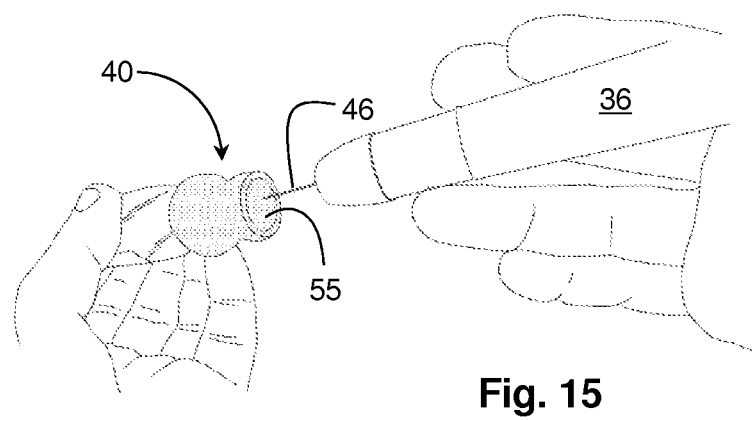
FIGS. 15 and 16 show use of the collar to avoid the risk of self-injection or damage when transferring liquid between the bottle and a hypodermic syringe.
Figure 16:
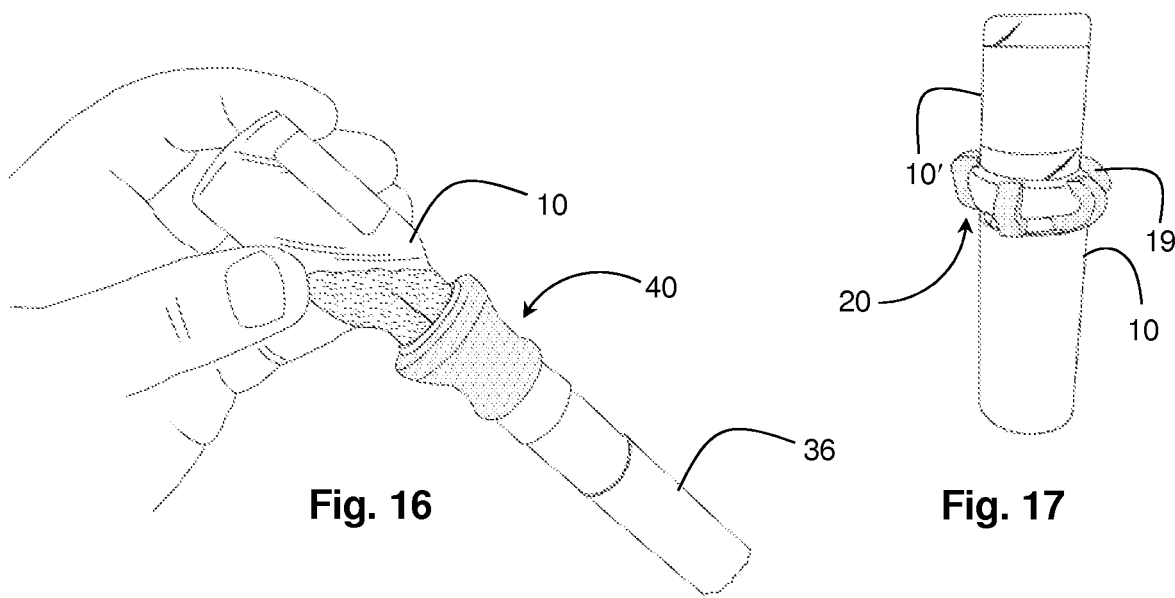

FIG. 15 shows another embodiment where this risk is avoided altogether by elongating the collar 40 and providing at its end an internal axial bore 55 configured to accommodate an end of the hypodermic syringe 36, thus allowing the neck of the bottle 10 to be coupled to the hypodermic syringe 36 as shown in FIG. 12. By such means the collar 40 serves both as a grip and a sleeve or coupler for coupling to the mouth of another utensil as shown in FIG. 16.

Figure 17:
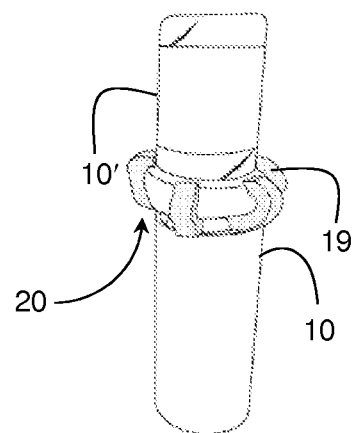
FIG. 17 shows use of the bottle support to effect limited coupling between the bottle and another utensil.

FIG. 17 shows use of the bottle support 20 to effect limited coupling between the bottle 10 and another utensil 10'. Thus, when the bottle 10 is inserted into the bottle support 20, the depth of the ribs 19 at their lower ends creates a recess 32 shown in FIG. 5c. It will be appreciated that the depth of the recess depends on the dimensions and geometry of the ribs, specifically how far they extend beneath the base of the bottle support. But it also may be a function of their overall length and thickness and even their resilience since these factors will determine how far the bottle 10 needs to be pushed down into the bottle support to be firmly supported thereby. If the ribs are sufficiently stiff to support the bottle without the need to push the bottle down fully, this allows the effective depth of the recess 32 to be increased.

We have described so far multiple uses of the bottle support and the collar, both independently and in combination. We now describe further optional features of the collar which have particular application to its use with hypodermic syringes and ameliorate the drawbacks discussed above.

Figure 18:
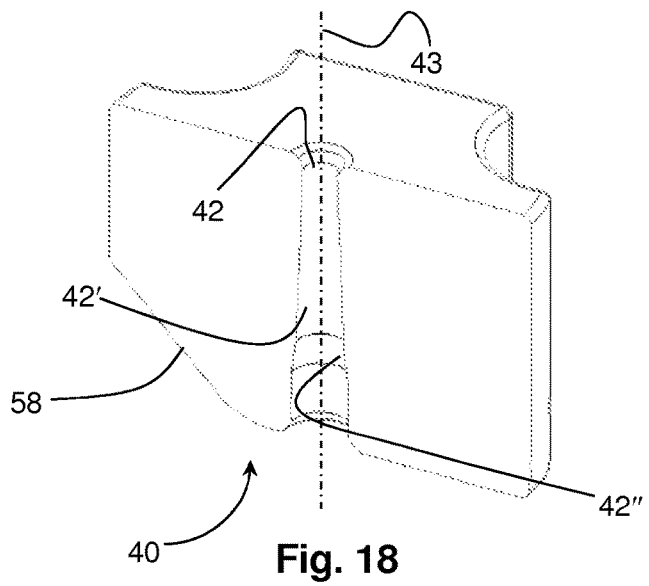
FIG. 18 shows in cross-section a collar having a slanted surface for guiding a hypodermic syringe.

FIG. 18 shows in cross-section a collar 40 having a bore 42 shaped for accommodating the end of a hypodermic syringe (not shown) as described above with reference to FIG. 10b. One side face 58 of the collar is at least partially beveled or slanted at an angle of 15° so that in use when this surface is guided along the surface of a patient's skin, the needle (not shown) will be maintained at an appropriate angle for venous injection without the need for manual support by the operator's finger. It should be noted that the drawing is schematic and in practice the slanted edge will be toward the front of the collar as shown by the chain-dotted lines in FIG. 10b.

Figure 19:
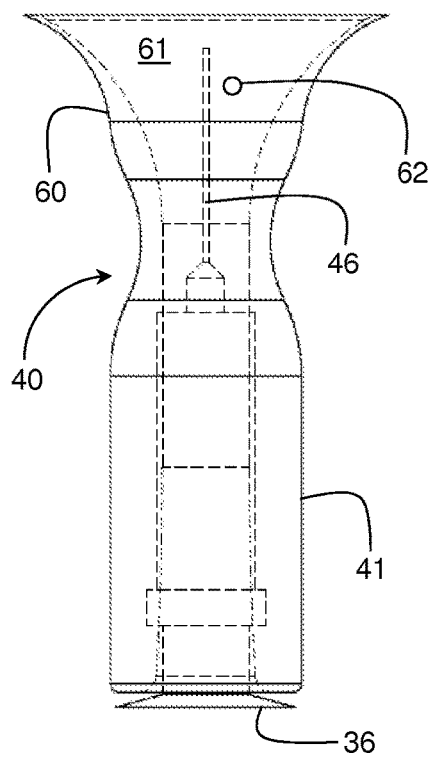
FIG. 19 shows in cross-section a collar fitted over the operative end of a hypodermic syringe for shielding the needle.

FIG. 19 shows in cross-section a collar 40 whose body 41 has an axial bore shaped to accommodate the operative end of a hypodermic syringe 36 and having a front end 60 for shielding the needle 46. The front end 60 is flared to provide a peripheral flexible skirt 61 that is formed of thin elastic material that is dimensioned such that in the initial state prior to use it completely covers and conceals the needle, but axially deforms when pushed against the surface of a patient's skin so as to retreat as the needle is injected. In order to prevent the flexible skirt 61 sticking to the patient's skin, breathing apertures 62 are provided around the periphery of the skirt that admit air and hinder suction. Alternatively, the flexible skirt 61 may be dimensioned so that that in the initial state prior to use the needle protrudes a predetermined length.

Figure 20:
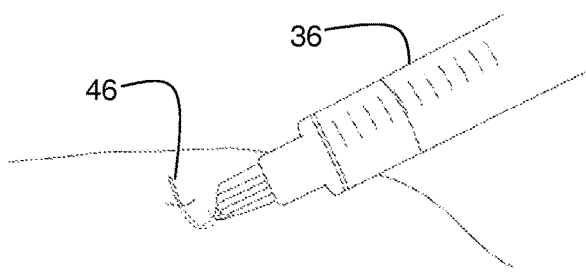
FIG. 20 shows bending of a hypodermic needle that may occur with conventional syringes.

The extent to which the needle 46 protrudes in the default state directly impacts on its tendency to bend. Hypodermic needles are very thin and easily deformed. If they are injected at the wrong angle and/or the patient moves, the needle can bend as shown in FIG. 20 and puncture the patient's skin in two locations. This is both painful and ineffective because the contents of the syringe are wasted and thus requires a further injection.

Figure 21:
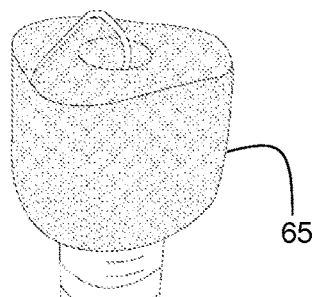
FIG. 21 shows pictorially a resilient collar that reduces the malfunction shown in FIG. 20.
Figure 22:
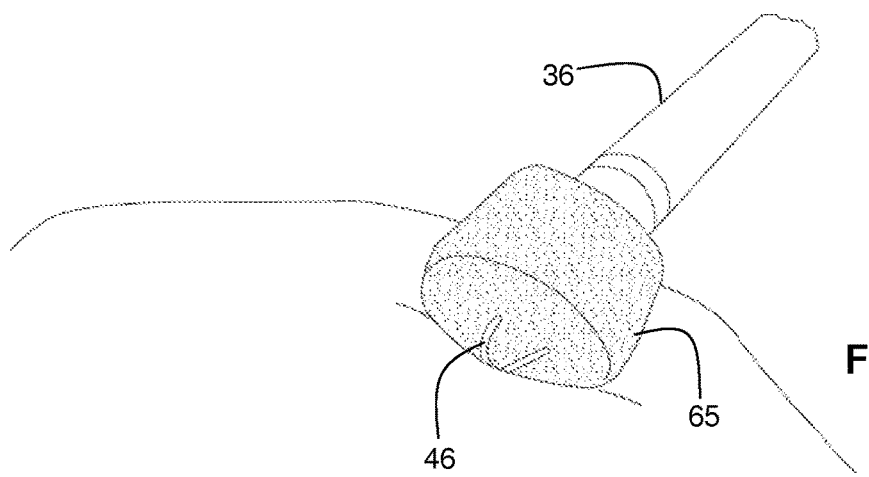
FIG. 22 shows pictorially how the collar of FIG. 21 cushions the needle and prevents it from bending inside the patient's skin.
Figure 23A:
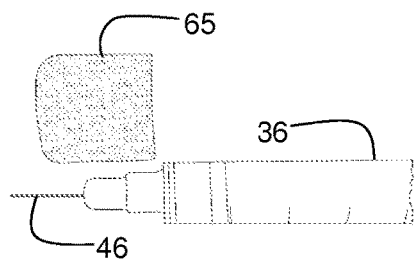
FIGS. 23a and 23b show respectively details of a hypodermic syringe before and after the collar of FIG. 21 is fitted over the needle.
Figure 23B:
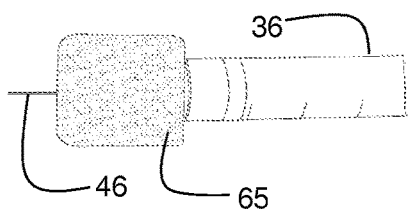
Figure 24A:
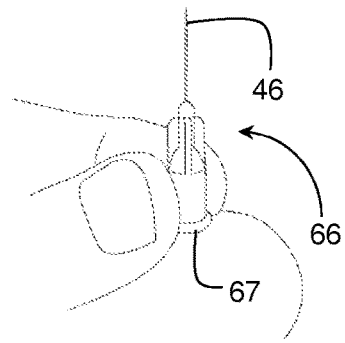
FIG. 24a shows a detail of a prior art needle assembly.
Figure 25:
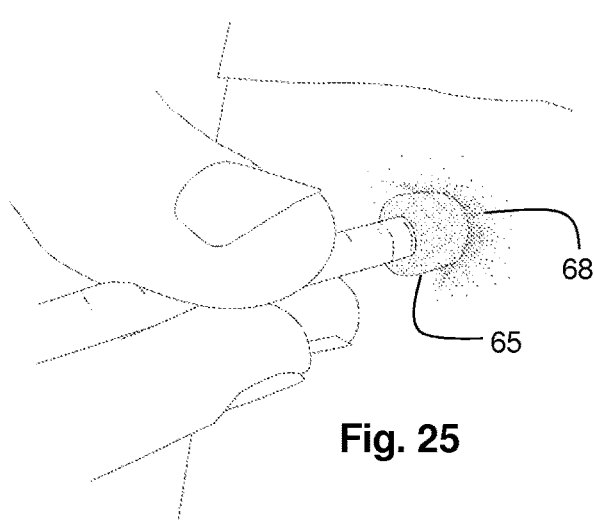
FIG. 25 shows the effect of using the collar to spread the pressure over a wider area.
Figure 24B:
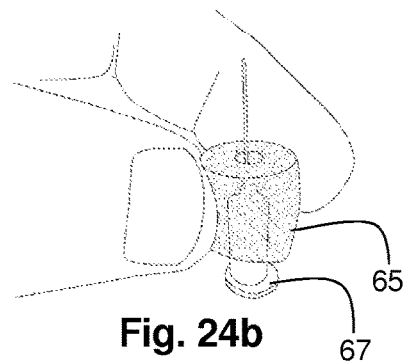
FIG. 24b shows pictorially how the collar of FIG. 21 is fitted on to such a needle assembly.
Figure 26A:
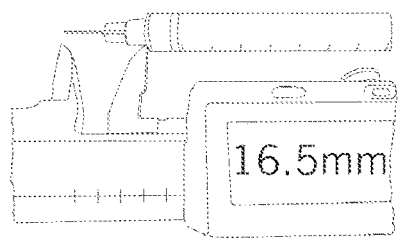
FIGS. 26a, 26b and 26c show typical dimensions associated with the needle assembly with and without the collar in situ.
Figure 26B:
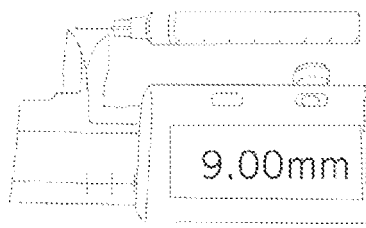
Figure 26C:
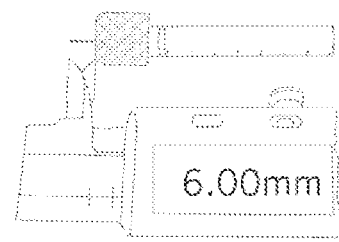

FIG. 21 shows how this malfunction can at least be mitigated by use of a collar 65 formed of deformable material such as foam and dimensioned for axial compression or displacement of a predetermined distance that is adjusted to define a known protrusion of a hypodermic needle. In this embodiment, the collar has a solid base portion that serves as a cap. FIG. 22 shows use of the collar 65, which abuts the skin as the needle 46 is injected. Should the needle bend owing to slight misalignment, it is cushioned by the collar and will bend back on itself without penetrating the patient's skin. FIGS. 23a and 23b show respectively details of the hypodermic syringe before and after the collar 65 is fitted over the needle. FIG. 24a shows a detail of a needle assembly 66 having a base 67 supporting the needle 46. FIG. 24b shows the collar 65 as it is fitted on to the needle assembly 66 so as to be supported by a peripheral flange of the base with the needle protruding through the opposite end of the collar. FIG. 25 shows the effect of using the collar 65, which pushes against the surface of the patient's skin over an extended area 68 thereof, which spreads the pressure over a wider area thereby reducing pain and assists in distributing the contents of the syringe more quickly through the surrounding tissue. FIGS. 26a, 26b and 26c show respectively typical dimensions of the needle assembly 66 (16.5 mm), and the length of the protruding end of the needle 46 without (9 mm) and with (6 mm) the collar in situ.

In all embodiments, the collar may be integral with the object or utensil to which it is coupled. So, for example, it may be integral with the bottle allowing easy coupling to the hypodermic syringe, or vice versa.

Figure 27A:
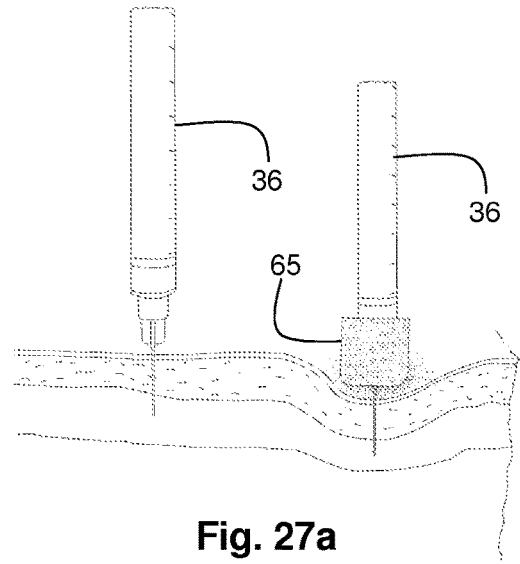
FIGS. 27a, 27b and 27c show pictorially comparisons of prior art syringes with a syringe fitted with the collar of FIG. 21.
Figure 27B:
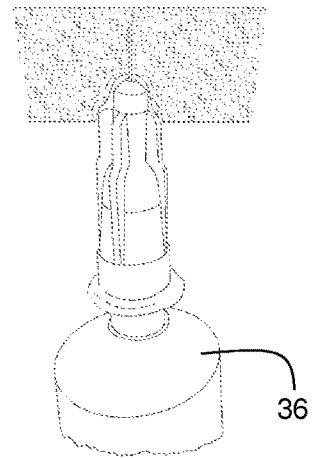
Figure 27C:
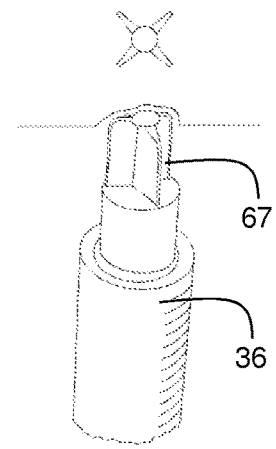

FIGS. 27a, 27b and 27c show pictorially comparisons of prior art syringes with a syringe fitted with the collar of FIG. 21. Thus as best seen in FIGS. 27b and 27c the operative end of the hypodermic syringe has two intersecting ridges that press into the skin if pushed too deeply, causing significant pain to the patient. In contrast thereto, the resilient collar 65 cushions the impact and helps to distribute pressure and thereby reduces pain.

Figure 28:
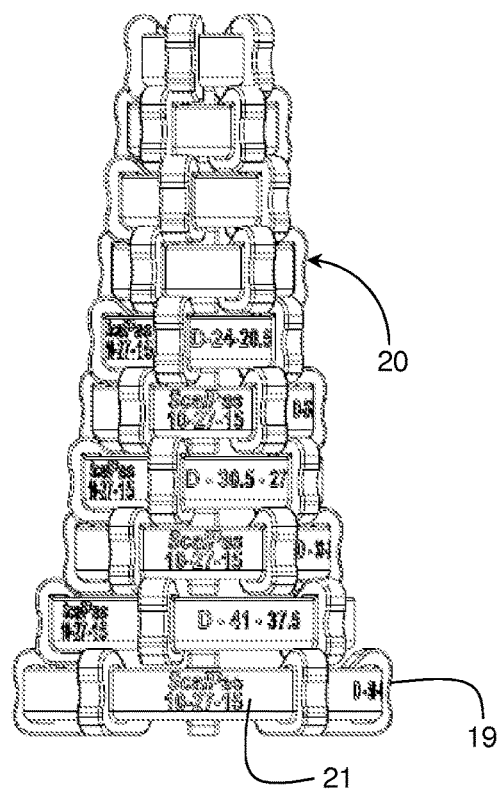
FIG. 28 shows pictorially multiple bottle supports stacked for easy display and packing.

FIG. 28 shows pictorially multiple bottle supports 20 of different diameters stacked for easy display and packing. Preferably, the annular core 21 of each bottle support is dimensioned so that when stacked on top of an immediately adjacent bottle support of larger diameter, the annular core 21 of the upper bottle support is supported by the ribs 19 of the lower bottle support, while the ribs of the upper bottle support are supported by the annular core of the lower bottle support. Even more preferably, the annular cores 21 are dimensioned so that any two alternate bottle supports can be stacked flat. In other words, the outer edges of the ribs 19 of the smaller bottle support fit snugly within the inner edges of the ribs 19 of the lower bottle support. In this case, multiple bottle supports can either be stacked into a tower as shown in FIG. 28 or they be dismantled and reassembled to form two sets of concentric rings.

Figure 29A:
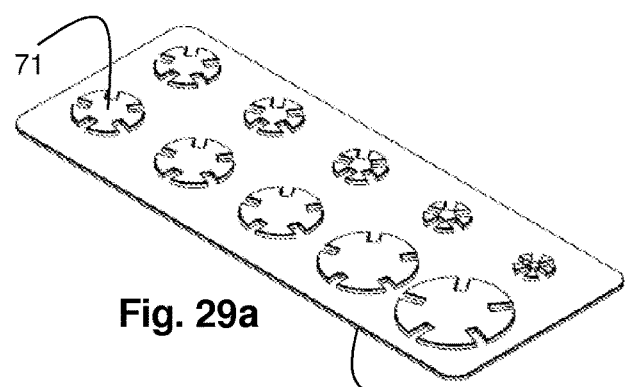
FIG. 29a shows pictorially a tray for mounting multiple bottle supports.
Figure 29B:
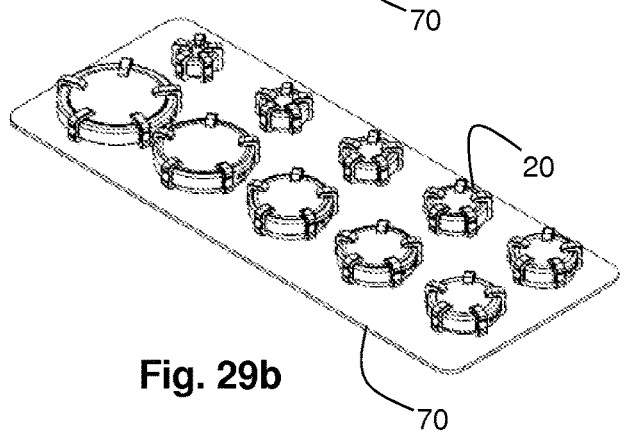
FIG. 29b shows pictorially use of such a tray to mount multiple bottle supports.

FIG. 29a shows pictorially a tray 70 for mounting multiple bottle supports 20. The tray 70 has a plurality of upraised protuberances each dimensioned for accommodating a bottle support of appropriate diameter as shown in FIG. 29b.

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

It will also be appreciated that while the first aspect of the invention has been described with particular reference to a bottle support and the second aspect with particular reference to a collar for a hypodermic syringe, these are not intended to be limiting applications. Thus, the bottle support may more generally be a mount for supporting any cylindrical object and the collar may likewise be used in conjunction with any cylindrical object. In both cases as noted previously the object does not need to have a circular or even uniform cross-section.

The invention claimed is:

1. A mount for supporting a utensil, the mount comprising:
    an annular core having an inner side surface defining a hollow opening, an outer side surface, a top surface and a base surface, and
    a plurality of pliable ribs, each at least partially encircling the annular core so as to overlap the outer side surface, the top surface and the base surface, while leaving the inner side surface of the annular core exposed between an upper and a lower end of said each respective pliable rib, and wherein at least the upper end of each said pliable rib, where each said pliable rib overlaps the top surface, has a respective free end tip that extends into the hollow opening, and wherein said pliable ribs are peripherally spaced apart along the outer side surface of the annular core, and wherein an interior surface region of each of said pliable ribs, which is midway between the top surface and the base surface, overlaps the outer side surface of the annular core as to be flush with the outer side surface, and
    wherein a respective lower end of at least two of the said pliable ribs has a respective free end tip that extends into said hollow opening.

2. The mount according to claim 1, wherein said pliable ribs are formed of a composite C-shaped molding.

3. The mount according to claim 1, wherein the annular core is formed of an elastic material.

4. An assembly comprising
    a collar;
    the mount of claim 1; and
    a utensil, to which the collar and mount are each connected; and
    the collar comprises:
    a body portion having an internal axial bore for surrounding the utensil and defining along at least a portion of an axis thereof a substantially quadrilateral cross-section having in each corner thereof a respective arcuate recess.

5. The assembly according to claim 4, wherein the utensil is a hypodermic syringe, and the axial bore is configured to accommodate an end of the hypodermic syringe.

6. The assembly according to claim 5, wherein the axial bore includes at least two mutually contiguous sections of different cross-sectional areas.

7. The assembly according to claim 5, wherein the collar is formed of deformable material and is dimensioned for axial compression or displacement of a predetermined distance that is adjusted to define a known protrusion of a hypodermic needle of the hypodermic syringe.

8. The assembly according to claim 4, wherein an outer surface of the body portion of the collar has a tapered portion that projects axially upward opposite a base portion of the collar.

9. The assembly according to claim 8, wherein an upper surface of the tapered portion is of smaller cross-sectional area than the base portion.

10. The assembly according to claim 8, wherein an upper surface of the tapered portion is of larger cross-sectional area than the base portion.

11. The assembly according to claim 10, wherein the tapered portion is formed of flexible material and forms a resilient skirt.

12. The assembly according to claim 11, wherein the tapered portion is dimensioned for axial compression of a predetermined distance that is adjusted to define a known penetration of a hypodermic needle.

13. The assembly according to claim 11, wherein the resilient skirt contains one or more apertures to inhibit suction when pressed against a skin surface.

14. The assembly according to claim 4, wherein the body portion is solid.

15. The assembly according to claim 14, where the body portion has a beveled indent.

16. The assembly according to claim 4, wherein the body portion of the collar is of rectangular cross-section, thus defining a pair of opposing first side surfaces and a pair of opposing second side surfaces, the first side surfaces being wider than the second side surfaces.

17. The assembly according to claim 16, where at least one of the first side surfaces has an elongated indent having a major axis normal to an axis of the body portion.

18. The assembly according to claim 4, wherein the collar and each of the annular core and said pliable ribs of the mount are formed of a pliable material.

19. A mount for supporting a utensil, the mount comprising:
  an annular core having an inner side surface defining a hollow opening, an outer side surface, a top surface and a base surface, and
  a plurality of pliable ribs, each at least partially encircling the annular core so as to overlap the outer side surface, the top surface and the base surface, while leaving the inner side surface of the annular core exposed between an upper and a lower end of each respective rib, and wherein at least the upper end of said each pliable rib, where each pliable rib overlaps the top surface, has a respective free end tip that extends into the hollow opening, and wherein said pliable ribs are peripherally spaced apart along the outer side surface of the annular core, and wherein an interior surface region of each of said pliable ribs, which is midway between the top surface and the base surface, is flush with the outer side surface,
  wherein the annular core and said pliable ribs are formed of a composite molding of pliable material.

20. A mount for supporting a utensil, the mount comprising:
  an annular core having an inner side surface defining a hollow opening, an outer side surface, a top surface and a base surface, and
  a plurality of pliable ribs, each at least partially encircling the annular core so as to overlap the outer side surface, the top surface and the base surface, while leaving the inner side surface of the annular core exposed between an upper and a lower end of each respective said pliable rib, and wherein at least the upper end of each said pliable rib, where each said pliable rib overlaps the top surface, has a respective free end tip that extends into the hollow opening, and wherein said pliable ribs are peripherally spaced apart along the outer side surface of the annular core, and wherein the annular core is continuous and non-interrupted in a natural state, and is formed of a pliable material, and
  wherein a respective lower end of at least some of said pliable ribs has a respective free end tip that extends into said hollow opening.

21. A mount for supporting a utensil, the mount comprising:
  an annular core having an inner side surface defining a hollow opening, an outer side surface, a top-most surface and a base surface, and
  a plurality of pliable ribs, each at least partially encircling the annular core so as to overlap the outer side surface, the top-most surface and the base surface such that at least an upper end of each rib, where each rib overlaps the top-most surface, has a respective free end tip that extends into the hollow opening, and wherein said pliable ribs are peripherally spaced apart along the outer side surface of the annular core, and wherein portions of the outer side surface of the annular core, that are between said pliable ribs, are exposed, and wherein portions of the inner side surface of the annular core falling below, on a common vertical axis, said respective free end tips of said pliable ribs are also exposed, and wherein the outer side surface of the annular core has a continuous surface extending from the top-most surface to the base surface, wherein said continuous surface has a common configuration as that of an interior surface of each of said pliable ribs that overlaps the outer side surface.

* * * * *